(12) United States Patent
Yamada

(10) Patent No.: US 10,251,639 B1
(45) Date of Patent: Apr. 9, 2019

(54) MENISCUS REPAIR SYSTEM

(71) Applicant: Ronald Yamada, Orangevale, CA (US)

(72) Inventor: Ronald Yamada, Orangevale, CA (US)

(73) Assignee: Ronald Yamada, Manteca, CA (US)

( * ) Notice: Subject to any disclaimer, the term of this patent is extended or adjusted under 35 U.S.C. 154(b) by 110 days.

(21) Appl. No.: 14/947,488

(22) Filed: Nov. 20, 2015

(51) Int. Cl.
*A61B 17/32* (2006.01)
*A61B 17/04* (2006.01)

(52) U.S. Cl.
CPC ...... *A61B 17/0482* (2013.01); *A61B 17/0401* (2013.01); *A61B 17/0469* (2013.01); *A61B 2017/0409* (2013.01)

(58) Field of Classification Search
CPC . A61B 17/0469; A61B 17/0482; A61B 17/88; A61B 2017/0496; A61B 2017/06042
See application file for complete search history.

(56) References Cited

U.S. PATENT DOCUMENTS

| | | | |
|---|---|---|---|
| 4,493,323 A * | 1/1985 | Albright | A61B 17/0469 606/144 |
| 5,391,182 A * | 2/1995 | Chin | A61B 17/0469 128/898 |
| 2,702,462 A | 12/1997 | Oberlander | |
| 6,638,286 B1 * | 10/2003 | Burbank | A61B 17/0469 606/139 |
| 7,232,448 B2 | 6/2007 | Battles et al. | |
| 7,608,092 B1 | 10/2009 | Schaffhausen | |
| 7,918,868 B2 * | 4/2011 | Marshall | A61B 17/0469 606/139 |
| 8,672,955 B2 * | 3/2014 | Nagata | A61B 17/0482 606/139 |
| 9,439,643 B2 * | 9/2016 | Darois | A61B 17/0057 |
| 2006/0190042 A1 | 8/2006 | Stone et al. | |
| 2008/0228204 A1 * | 9/2008 | Hamilton | A61B 17/0491 606/148 |
| 2009/0228041 A1 * | 9/2009 | Domingo | A61B 17/0469 606/223 |
| 2009/0312792 A1 | 12/2009 | Fallin et al. | |
| 2010/0228271 A1 * | 9/2010 | Marshall | A61B 17/0469 606/144 |
| 2010/0305583 A1 * | 12/2010 | Baird | A61B 17/0469 606/144 |
| 2011/0016076 A1 | 1/2011 | Howard et al. | |
| 2011/0022061 A1 | 1/2011 | Orphanos et al. | |
| 2011/0046646 A1 * | 2/2011 | Marshall | A61B 17/0469 606/145 |
| 2011/0112556 A1 | 5/2011 | Saliman et al. | |
| 2012/0283750 A1 | 11/2012 | Saliman et al. | |

FOREIGN PATENT DOCUMENTS

JP 478168989 7/2011

* cited by examiner

*Primary Examiner* — Julie A Szpira
(74) *Attorney, Agent, or Firm* — Haynes and Boone, LLP

(57) ABSTRACT

A device for repair meniscus tears utilizing transfer cannulas that are pulled or kedged through the meniscus tear by a pulling element. The transfer cannulas are positioned via sliding guide to prevent a shear force acting on the meniscus.

6 Claims, 14 Drawing Sheets

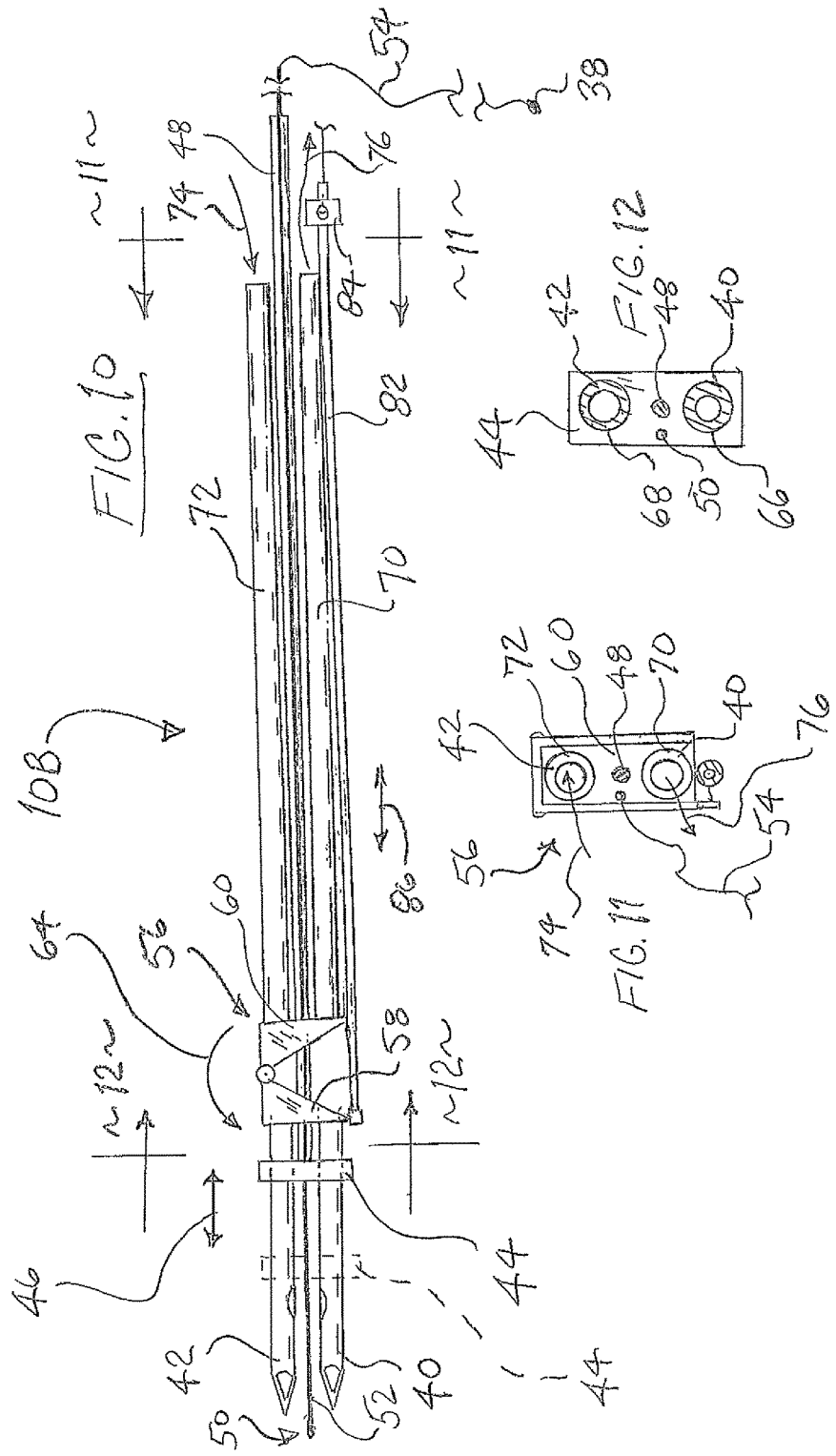

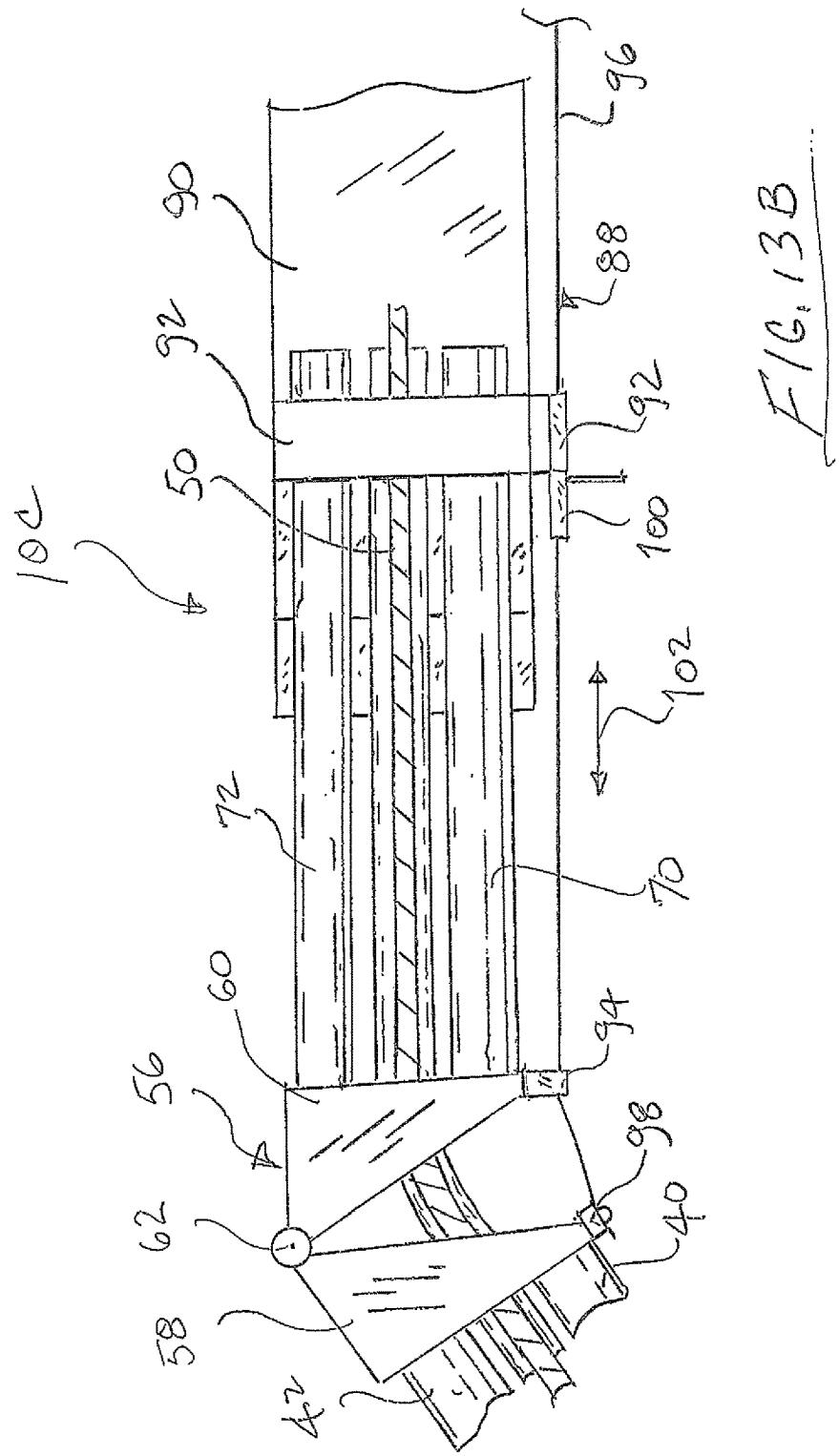

MENISCUS REPAIR SYSTEM

BACKGROUND OF THE INVENTION

The present invention relates to a novel and useful meniscus tear repair device and method.

The knee is the largest joint in the human body. Cartilage within the human knee joint protects the joint from stresses resulting from walking, running, climbing, bending and the like. The medial and lateral menisci comprise two large C-shaped cartilages that are positioned on the top of the tibia.

A torn meniscus occurs due to trauma caused by forceful twisting or hyper-flexing of the knee joint. A torn meniscus produces symptoms of knee pain, swelling, popping and giving way of the knee joint. Although treatment of a torn meniscus may include physical therapy and muscle strengthening to stabilize the knee joint, surgery to repair or remove the damaged cartilage is often the only effective treatment.

Depending on the meniscus tear pattern, surgical repair procedures may include the use of anchors, darts, or sutures. Meniscal repair options include outside-in, inside-out, and all-inside techniques. The all-inside suture system appears to be preferable in that the placement of a suture ultimately results in a strong repair and minimizes damage to major nerves and large blood vessels. In general, suture repairs has proven difficult to carry out because of the position of menisci and mechanical difficulties in placement of a suture that compresses and secures a torn meniscal tear. In addition, other problems due to the high pushing forces that are required to penetrate a meniscus using rigid cannulas and the undesirable creation of deforming shear forces at the tear by cannulas that are straight and rigid.

In the past, many systems and devices have been proposed to repair tissues and menisci within the knee. For example, U.S. Pat. No. 7,232,448, United States Patent Application Publication 2011/0112556, and U.S. Patent Application Publication 2012/0283750 describe specialized single cannulas utilizing movable components to pass a suture through tissue and return the same to provide a suture.

U.S. Pat. No. 5,702,462 describes a method and device for a meniscal repair employing a pair of darts that extend through the tear connected to sutures that are tied in a knot to tension the tear.

U.S. Pat. No. 7,608,092 and, United States Patent Application Publication 2009/0312792, United States Patent Application Publication 2011/0022061, United States Patent Application Publication 2006/0190042, and Japanese Patent 4781689B9 show meniscus repair devices that employ anchors which are passed through the meniscus tightened by connected sutures.

United States Patent Application Publication 2009/0228041, United States Patent Application Publication 2010/0228271, United States Patent Application Publication 2010/0305583 and United States Patent Application Publication 2011/016076 teach meniscal repair systems using straight rigid cannulas that penetrate the meniscus and include a transfer system to pass a suture through one cannula to the other cannula forming a knotted suture about the meniscus tear.

A meniscus tear repair device that allows a practitioner to pass suture repair cannulas through the meniscus tear without damage to meniscus or creating a deforming shear force at the meniscus repair site would be a notable advance in the medical arts.

SUMMARY OF THE INVENTION

In accordance with the present invention a novel and useful meniscus tear repair device and method is herein provided.

The invention includes as one of its elements a guide used in conjunction with first and second cannulas and a repair suture which is eventually transferred from the first to the second cannula. The guide possesses passageways for the first and second cannulas and allows a sliding relationship between the guide and the first and second cannulas. A bar is also provided and is fixed to the guide for movement therewith. The bar may be manually manipulated by the user of the device of the present invention to move the guide relative to the cannulas.

A support is also found in the present device and is fixed to the first and second cannulas. The support provides proper spacing and orientation of the cannulas. The bar slidingly engages the support during its movement with the guide. Thus, relative movement occurs between the support and the bar through a passageway that is formed in the support to allow such movement of the bar.

An elongated pulling element also constitutes an element of the device of the device of the present invention. The elongated pulling element may take the form of a pointed member, such as a needle, connected to a line. An elongated pulling element is capable of exerting a pulling force on the support and the fixed first and second cannulas. Thus, the guide and the support includes passageways for the elongated pulling element to allow passage of the pointed member and the line connected thereto.

In a further embodiment of the device of the present invention, the support may be formed with a first portion, a second portion, and a hinge between the first and second portions. The bar connected to the guide and the elongated pulling element are formed into flexible member to allow bending when the first and second portions are rotated relative to one another via the hinge. A moveable operator is connected to the first portion of the hinge to allow the user to hingedly move the first portion relative to the second portion of the support. A lock is also provided for arresting the movement of the moveable operator and, thus, the movement of the first portion relative to the second portion of the support. In this manner, the hinge support allows the user to better manipulate the first and second cannulas when effecting repair of a meniscus tear.

It may be apparent that a novel and useful surgical device intended for suturing anatomical meniscus tear has been herein above described.

It is thus an object of the present invention to provide a surgical device to repair meniscus tears which guides a pair of suture passing cannulas into a meniscus.

Another object of the present invention is to provide a surgical device for repairing a meniscus tear which avoids over-penetration of suture passing cannulas and subsequent entrapment of tissue.

Another object of the present invention is to provide a surgical device for repairing meniscus tears which eliminates the need for darts and anchors and provides for a "suture alone" repair system.

Another object of the present invention is to provide a surgical device for effecting repair of meniscus tears that avoids the application of shear forces at the meniscal tear by a pair of repair cannulas.

Another object of the present invention is to provide a surgical device for the repair of meniscus repairs that prevents twisting or bending of repair cannulas that may result in impeding of the transfer of a repair suture.

Another object of the present invention is to provide a surgical device for repairing meniscus tears that is capable of repairing mid-body, interior horn, and posterior horn meniscus tears.

A further object of the present invention is to provide a device for the repair of meniscus tears that easily avoids neurovascular structures during use.

A further object of the present invention is to provide a surgical device for repairing meniscus repairs that employs a pair of suture passing prongs having adjustable angulation when penetrating a meniscus.

A further object of the present invention is to provide a surgical device for repairing meniscus tears that allows the insertion of suture passing cannulas without the use of excessive force, thus avoiding meniscus buckling, over penetration, or device malfunction.

A further object of the present invention is to provide a surgical device intended for repairing meniscal tears that allows the approximate perpendicular insertion of repair cannulas relative to the tear.

Yet another object of the present invention is to provide a surgical device intended for the repair of meniscal tears that employs a kedging or pulling element to guide suture passing cannulas during an insertion into the meniscus.

The device of the present invention includes other objects and advantages especially as concerns particular characteristics and features thereof which will become apparent as the specification continues.

BRIEF DESCRIPTION OF THE SEVERAL VIEWS OF THE DRAWING

FIG. 10 is a top plan view of another embodiment of the present invention.

FIG. 11 is a sectional view taken along line 11-11 of FIG. 10.

FIG. 12 is a sectional view taken along line 12-12.

FIG. 13B is a partial enlarged top plan view of the device depicted in FIG. 10 as an extension to the right side of device 10C shown in FIG. 13A.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

Figure 1:
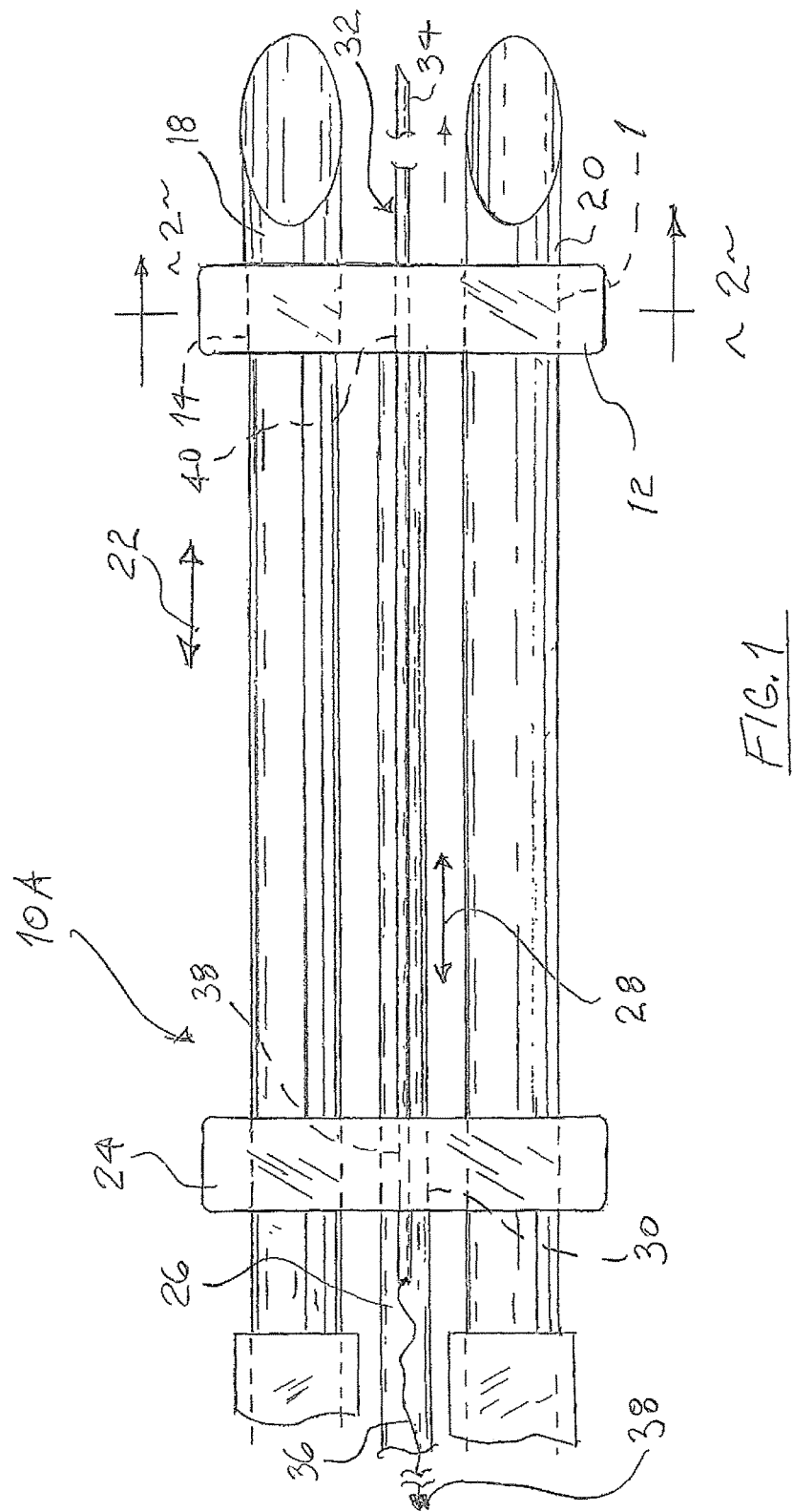
FIG. 1 is a top plan view of the first embodiment of the present invention.

Embodiments of the device of the present application are identified by reference character 10 followed by an upper case letter to denote variations of the same. With reference to FIG. 1, an meniscus repair device 10A is depicted. Device 10A includes as one of its elements a guide or guide block 12. Guide 12 may be formed of any rigid or semi-rigid material and includes passageways 14 and 16 for the sliding engagement of cannulas 18 and 20. Directional arrow 22 indicates the sliding movement of cannulas 18 and 20 relative to guide 12. Cannulas 18 and 20 are suture transferring cannulas using methods and devices of the prior art, which will be discussed as the specification continues.

Device 10A is also fashioned with a support 24 that is fixed to first and second cannulas 18 and 20. Support 24 provides spacing and orientation of cannulas 18 and 20 in device 10A.

Figure 2:
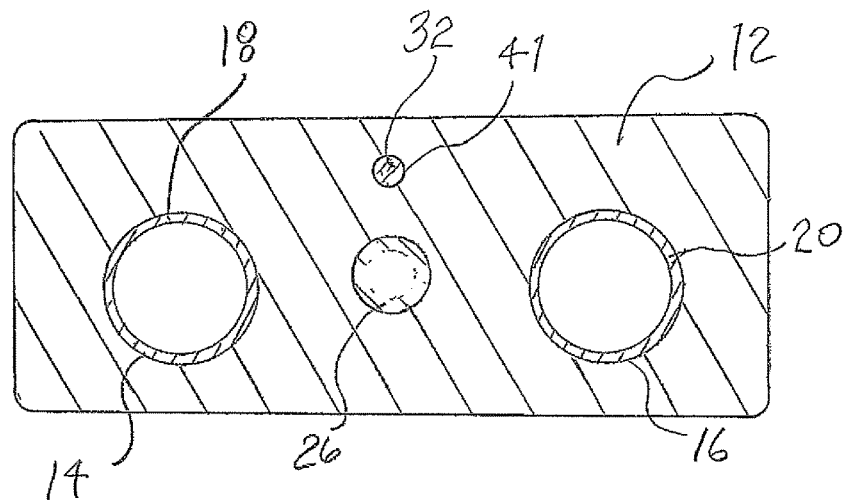
FIG. 2 is a sectional view taken along line 2-2 of FIG. 1.

A bar or guide rod 26 may also be found in device 10 and is fixed to guide 12 for movement therewith. Bar 26 slidingly engages support 24 and is intended as a push-pull device manipulated by the user of device 10A. Directional arrow 28 indicates the sliding movement between bar 26 and support 24. Although FIG. 2, represents a sectional view of guide 12, a similar sectional view of support 24 would have an identical appearance. Needless to say, a passageway 30 is formed through support 24 to allow the movement of bar 26 according to directional arrow 28. Consequently, the movement of bar 26 by the user of device 10A would also move connected or fixed guide 12 relative to cannulas 18 and 20.

In addition, device 10A is constructed with an elongated pulling element 32 having a pointed member 34, such as a needle, and a connected line 36. Line 36 terminates in an enlargement bead or knot 38. A passageway 41 through guide 12 permits the sliding movement of elongated pulling element 32 relative to support 24 and guide 12. Again, a passageway similar to passageway 41 extends through support 24 and allows such sliding movement, FIGS. 1 and 2.

Figure 13:
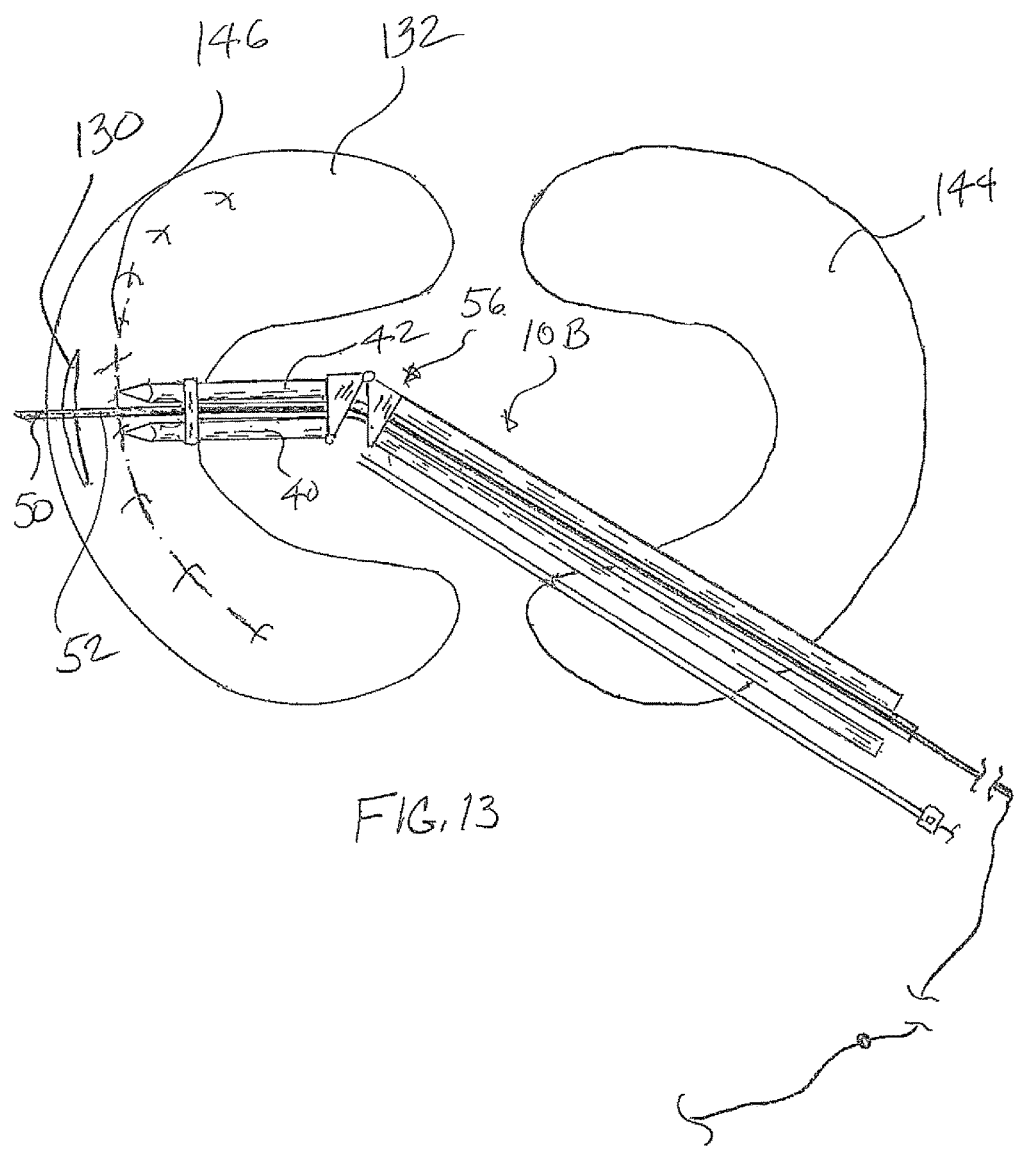
FIG. 13 is a schematic top plan view partially showing the device of FIG. 12 about to penetrate a meniscus to repair a tear.
Figure 13A:
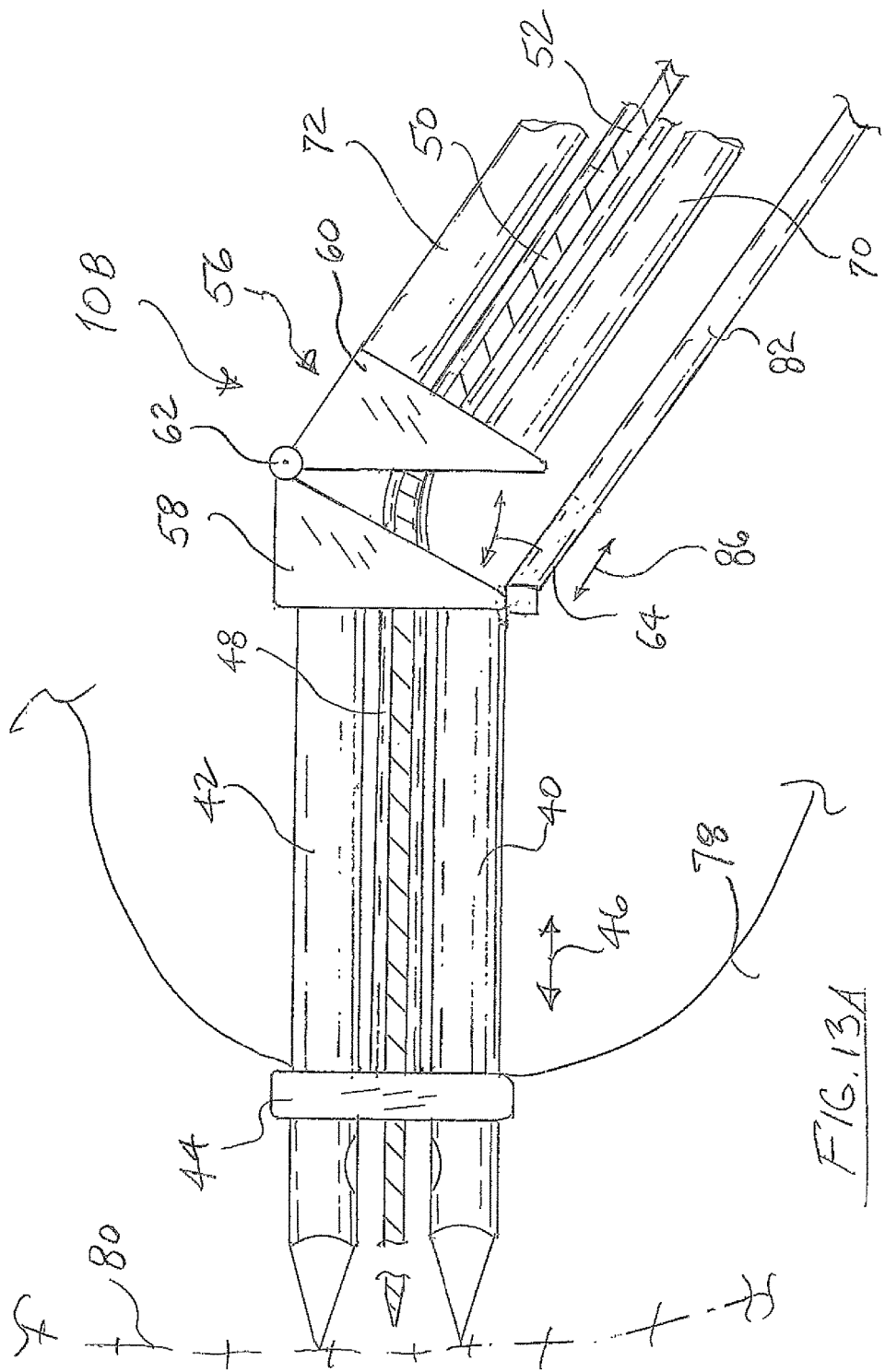
FIG. 13A is a partial enlarged top plan view of the device depicted in FIG. 10 adjacent a meniscus.

Turning now to FIGS. 10, 13A and 13B, it may be observed that another embodiment 10B of the device of the present application is shown. Device 10B is intended for use with suture transferring cannulas 40 and 42 which are slidably mounted relative to a guide 44. Such sliding is indicated by directional arrow 46 and the phantom rendition of guide 44 on FIG. 10. A push/pull bar or rod 48 is also found in embodiment 10B and is fixed to guide 44. Moreover, an elongated pulling element 50 is also shown on FIGS. 10-12. Again, an elongated pulling element 50 consist of a pointed member, such as a needle 52 and a line 54 connected thereto. Most importantly, embodiment 10B includes a support 56 that includes a first portion 58, a second portion 60, and a rotatable member or hinge 62. Hinge 62 may take many forms such as a ball and socket joint, a flexible member and the like. Thus, first portion hingedly rotates relative to second portion on support 56, best shown in FIGS. 13A and 13B. Consequently, push-pull bar 48 and elongated pulling element 50 comprise flexible members to accommodate the hinged movement between first and second portions 58 and 60, respectively according to directional arrow 64. It should be noted that needle 52 of elongated pulling element 50 is depicted in an enlarged configuration and in section on FIGS. 13A and 13B for the sake of clarity. Further, tubes 70 and 72, fixed to second portion 60 of support 56, serve as continuation of cannulas 40 and 42 and to help guide a repair suture which eventually passes into tube 72 through cannula 42, out cannula 40 and into tube 70, indicated by directional arrows 74 and 76 of FIG. 10.

Referring now to FIG. 13A a portion of a meniscus 78 having an upper or superior surface 80 is shown relative to device 10B. A moveable operator, in the form of a rigid shaft 82 having a lock 84 is depicted schematically on FIG. 10. Operator shaft 82 would move first portion 58 of support 56 relative to second portion 60 in order to angulate cannulas 40 and 42, relative to tubes 70 and 72. The detailed use of device 10B, will be described hereinafter. FIGS. 13A and 13B shows the bending of push-pull bar 48 and needle 52 in this regard. Directional arrow 86, FIGS. 10 and 13A illustrates the movement of operator shaft 82 to rotate hinge 62 and angulate cannulas 40 and 44 relative to tubes 70 and 72.

Turning now to FIG. 13B, it may be observed that another embodiment 10C of the present invention is shown that includes many of the components of embodiment 10B. Accordingly, support 56 is employed with tubes 72 and 70, cannulas 40 and 42, and elongated pulling element 50. However, embodiment 10B possesses an alternate hinge operator 88 and further includes a base 90 having a holder 92 for tubes 70 and 72 as well as for a sliding support for movable elongated pulling element 50. Guides 92 and 94 direct a semi-rigid band 96 to an anchor 98 connected to support 56. Band lock 100 releasable holds semi-rigid band 96 between hand lock 100 and anchor 98. In other words, semi-rigid band 96 can be adjusted bi-directionally as by directional arrow 102. Consequently, movement of band 96 hingedly moves first portion 58 relative to second portion 60 of support 56. Band 96 also adjusts the angulation between cannulas 40 and 42 and fixed tubes 70 and 72.

Figure 19:
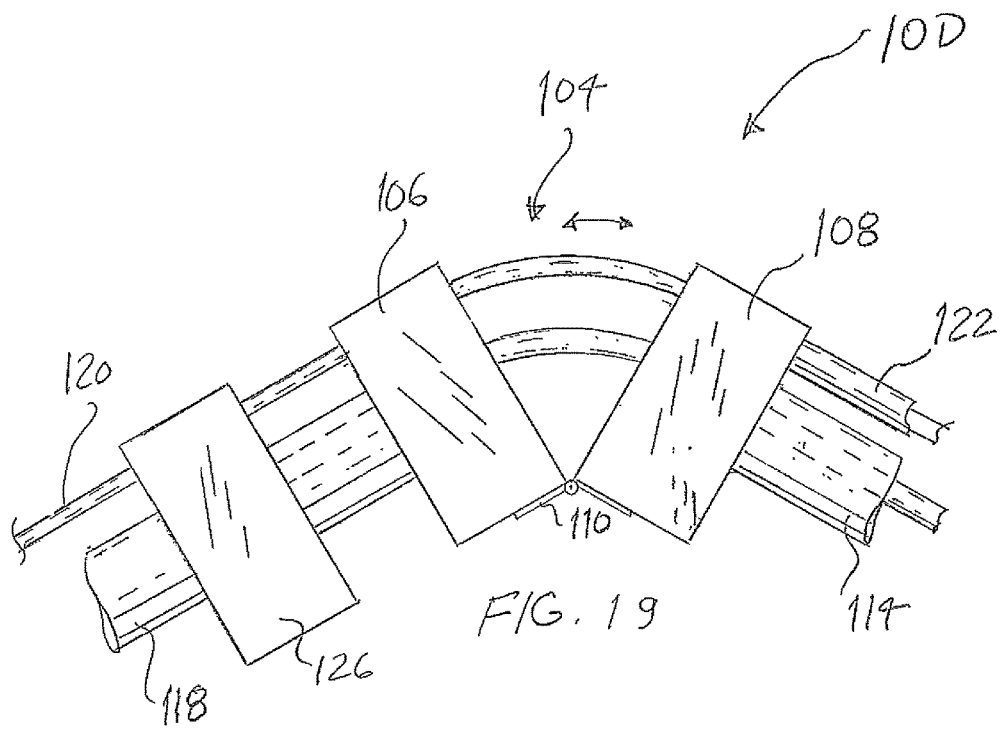
FIG. 19 is a partial top plan view of another embodiment of the present invention.
Figure 20:
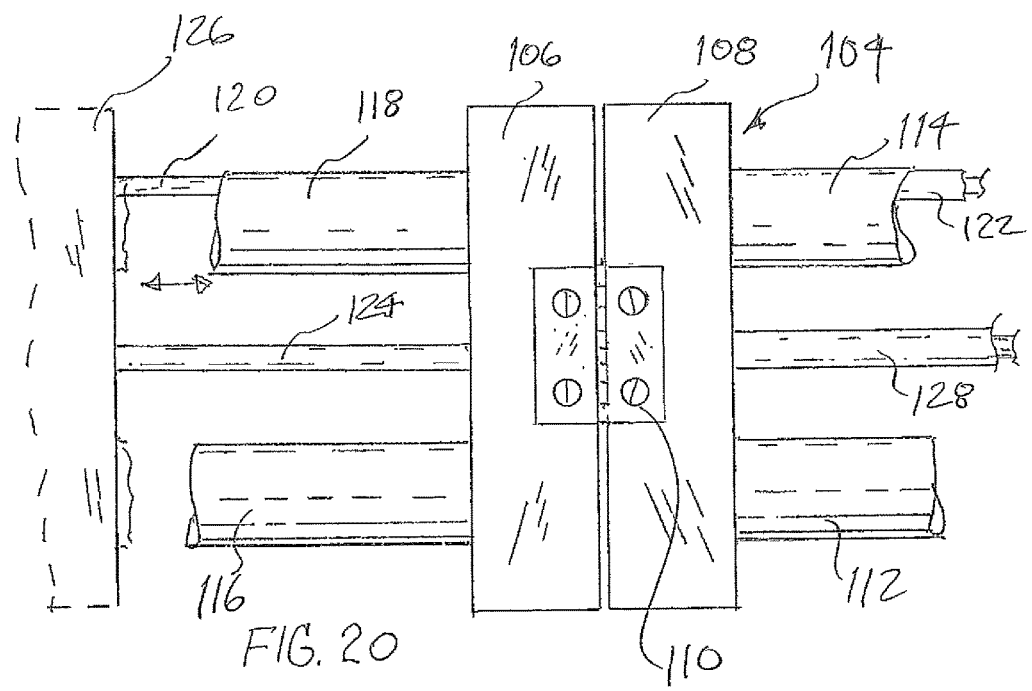
FIG. 20 is a side elevational view of the embodiment of the present invention depicted in FIG. 19.

Referring to FIGS. 19 and 20, it may be seen that another embodiment 10D of the device of the present application is depicted in which a hinged or rotatable support 104 is turned 90° from that shown in FIGS. 10, 13A and 13B. Hinged support 104 has a first portion 106, a second portion 108 and a hinge 110. Tubes 112 and 114 are held by first portion 108. Cannulas 116 and 118, capable of communicating with tubes 112 and 114, respectively, are held by first portion 106 of support 104. Flexible elongated pulling element 120 is encased in a sheath 122 prior to passage through second portion 108 of support 104. Flexible bar 124 connects to guide 126 and is also enclosed in a sheath 128 prior to passage through second portion 108 of support 104. A hinge operator and locking mechanism as shown in FIGS. 13A and 13B would also be used with the embodiment 10D depicted in FIGS. 19 and 20 (not shown).

Figure 3:
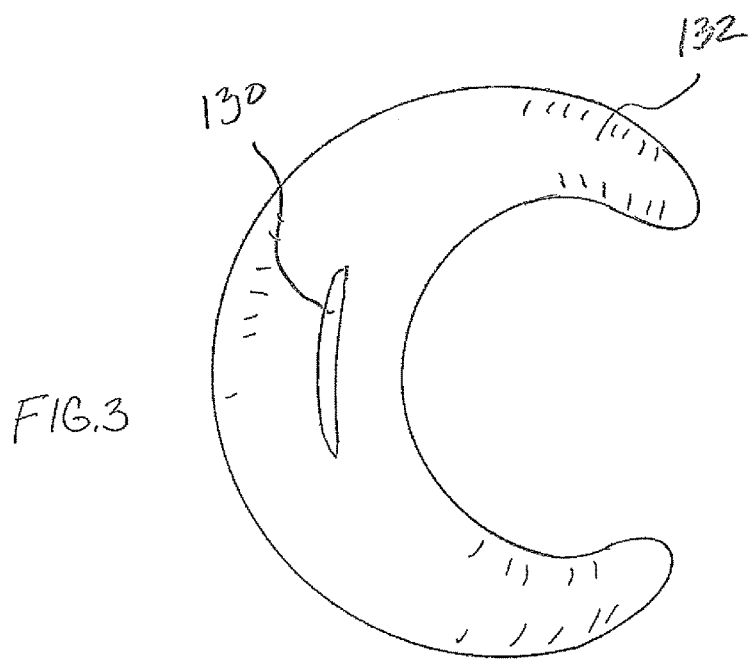
FIG. 3 is a top plan schematic view of a meniscus having a tear.
Figure 4:
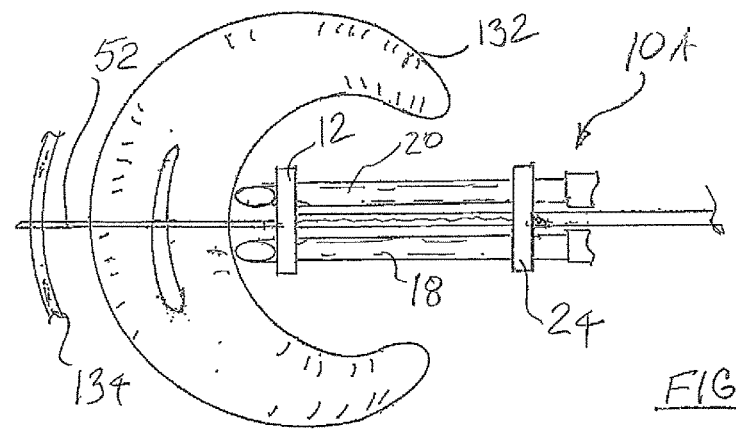
FIG. 4 is a schematic view of the device of FIG. 1 being employed to repair a meniscal tear.
Figure 5:
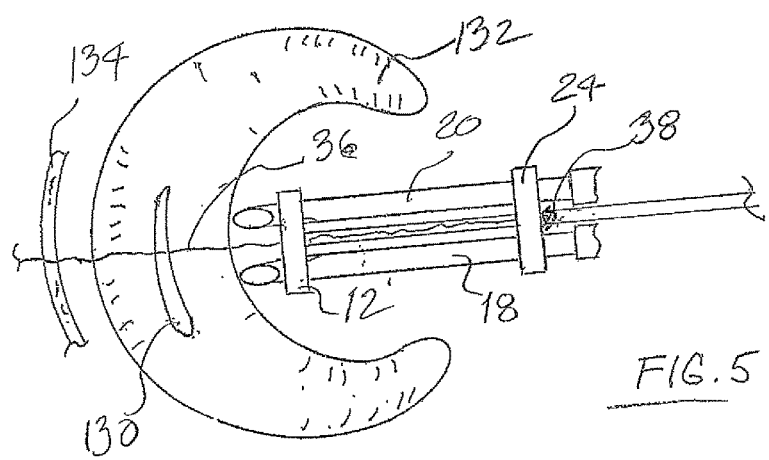
FIG. 5 is a schematic top plan view of the device of FIG. 1 being pulled through the meniscus depicted in FIG. 2.
Figure 6:
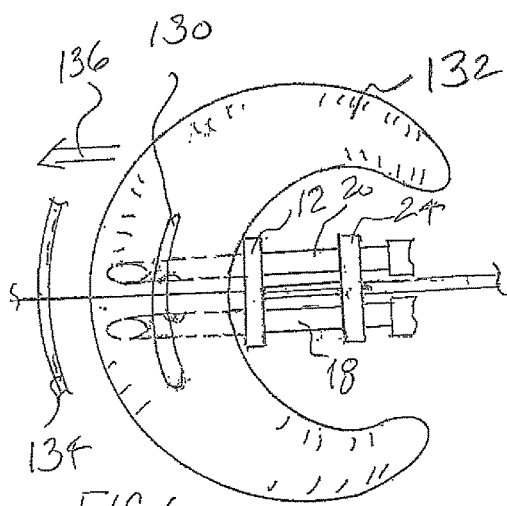
FIG. 6 is a schematic top plan view of the device of FIG. 1 having passed through the tear of the meniscus depicted in FIG. 2.
Figure 6A:
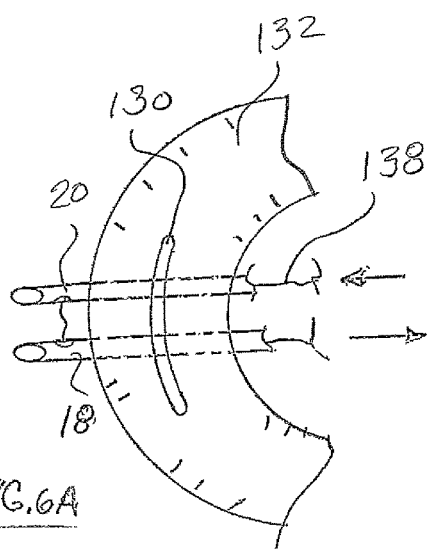
FIG. 6A is a partial schematic top plan view of the device of FIG. 1 having passed through the meniscal tear and meniscus, showing the repair suture being passed from one cannula to another.
Figure 7:
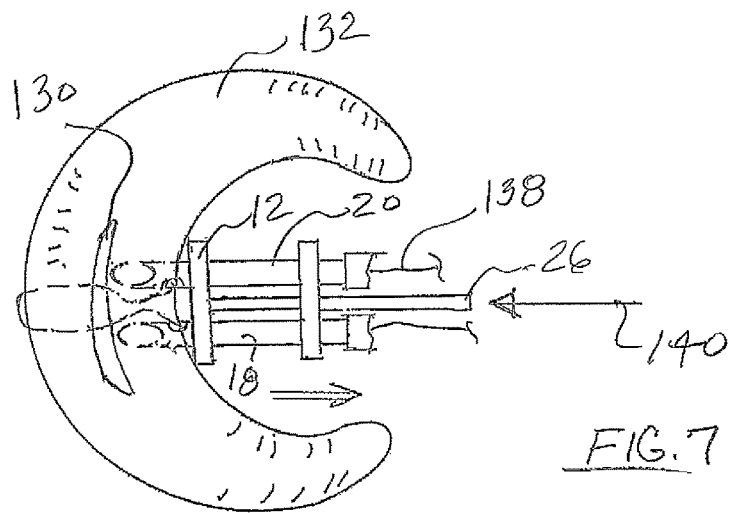
FIG. 7 is a schematic top plan view of the device of FIG. 1 being retracted from the meniscus of FIG. 3.
Figure 8:
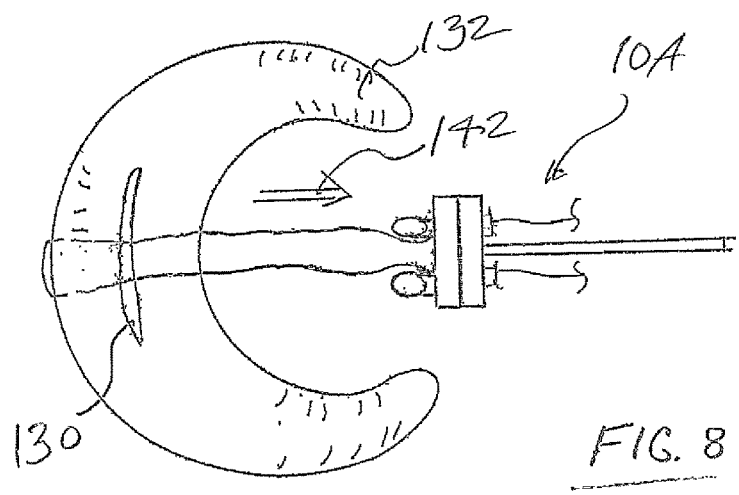
FIG. 8 is a schematic top plan view of the device of FIG. 1 having been removed from the meniscus of FIG. 2 with the repair suture in place.
Figure 9:
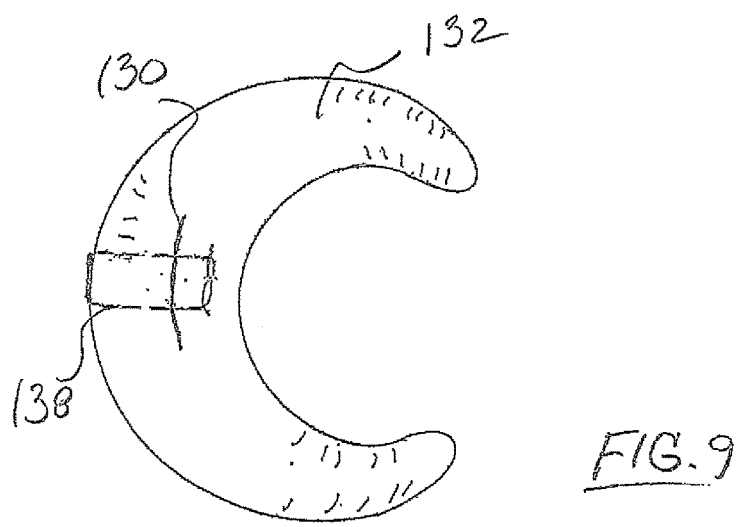
FIG. 9 is a schematic top plan view of the meniscus of FIG. 2 with the meniscal tear having been repaired with a suture tensioned by the device of FIG. 1.

In operation, embodiment 10A, depicted in FIGS. 1 and 2, may be employed to repair a meniscus tear 130 of meniscus 132, FIG. 3. As may be observed in FIG. 1 cannulas 18 and 20 extend from one end of device 10A. Referring now to FIGS. 4-9, it may seen that device 10A is inserted into the knee joint such that cannulas 18 and 20 lay adjacent meniscus 132 and at tear 130. Cannulas 18 and 20 are now oriented at an approximate right angle to the direction of elongation of tear 130. Guide 12 is then advanced toward tear 130. It should be noted that indicia or markings may be placed on cannulas 18 and 20 to indicate the relative position of guide 12 to cannulas 18 and 20. In this manner, the depth of penetration of cannulas 18 and 20 into meniscus 130 may be assessed. Elongated pulling element 50 is advanced across and through the tear 130. Needle 52 is further passed through the outer skin 134 of the knee, FIG. 4. Once outside the knee anatomy, needle 52 is detached and discarded, FIG. 5. Line 36 is then pulled, or kedged, which advances cannulas 18 and 20 into meniscus 132 and through tear 130, FIG. 6. At this point, knot 38 of line 136 engages support 24 allowing cannulas 18 and 20 to slide relative to guide 12. Directional arrow 136, FIG. 6, indicates the traction or kedging of device 10A through meniscus tear 130. It should be noted that elongated pulling element 32 and line 136 may pass over meniscus 132 or pass through the same. As shown in the drawings, elongated pulling element is passing over meniscus 132. Once cannulas 18 and 20 have passed through meniscus 132, a repair suture 138 may be passed from cannula 20 to cannula 18 by known techniques in the prior art, FIG. 6A. Bar or guide rod 26 is then pushed according to directional arrow 140 causing guide 12 to contact meniscus 130 and allowing cannulas 18 and 20 to retract from the meniscus 130. This action leaves repair suture 138 positioned through tear 130 of meniscus 132, FIG. 7. Device 10A is then completely removed from meniscus 132 according to directional arrow 142, FIG. 8. Suture 138 is subsequently tensioned, locked, and cut. Additional sutures such as repair suture 138, may be used to repair tear 130 if needed.

Figure 14:
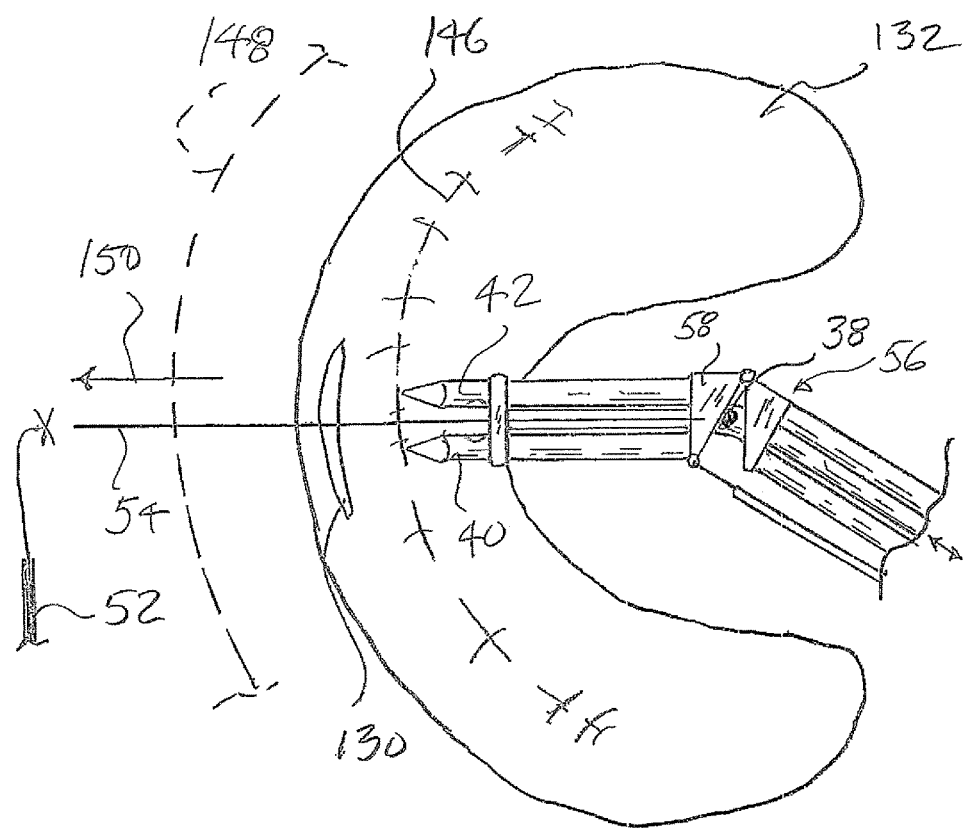
FIG. 14 is a schematic top plan view of the device of FIG. 10 having adjacent a meniscal tear with the kedging feature having been deployed.
Figure 15:
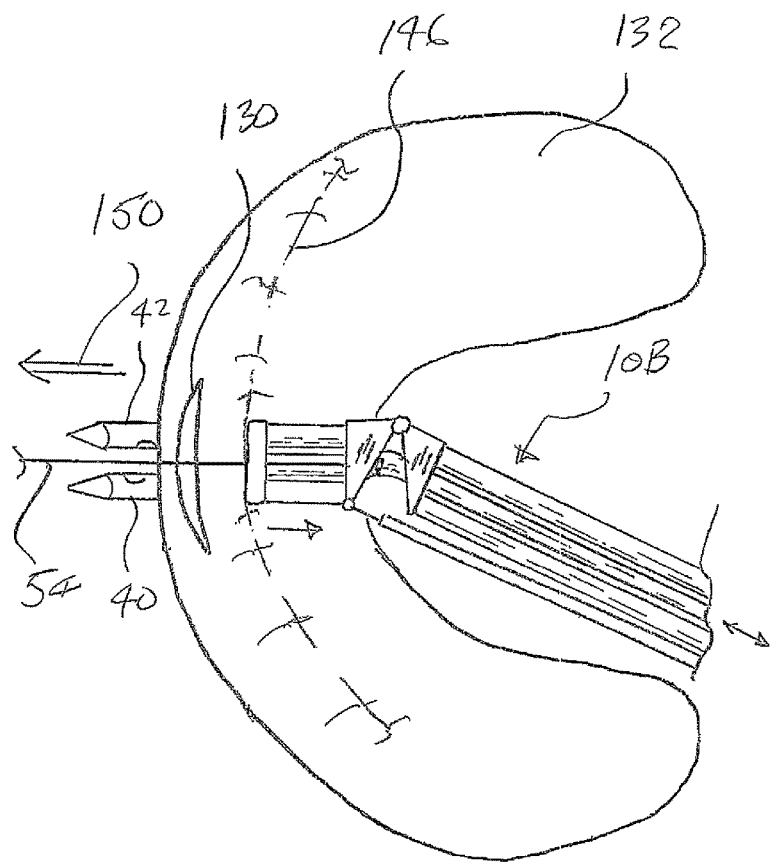
FIG. 15 is a schematic top plan view of the device of FIG. 10 having the repair suture cannulas being pulled through the meniscal tear and exiting the meniscus.
Figure 16:
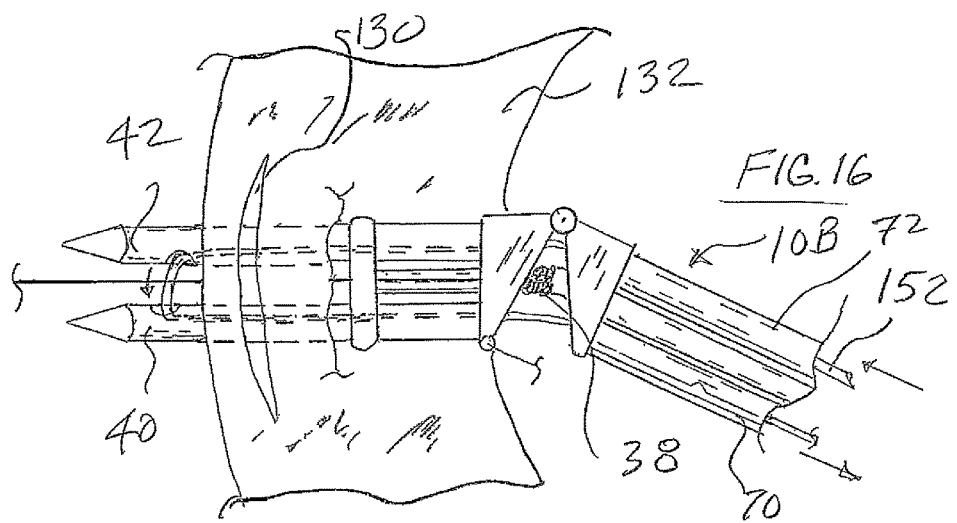
FIG. 16 is a schematic top plan view of the device of FIG. 10 showing the transfer of the repair suture between a pair of cannulas.
Figure 17:
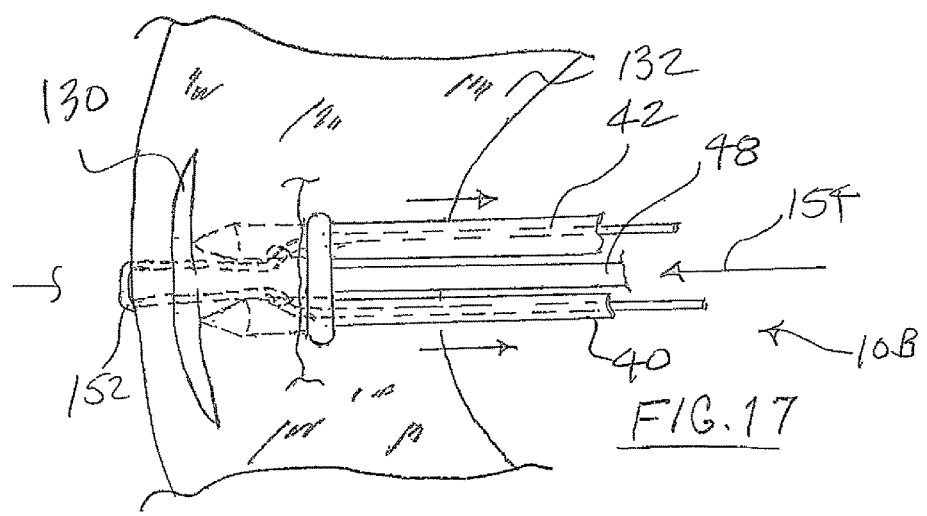
FIG. 17 is a schematic top plan view of the device of FIG. 10 in which the transferring cannulas are being removed from the meniscus, by force on the bar.
Figure 18:
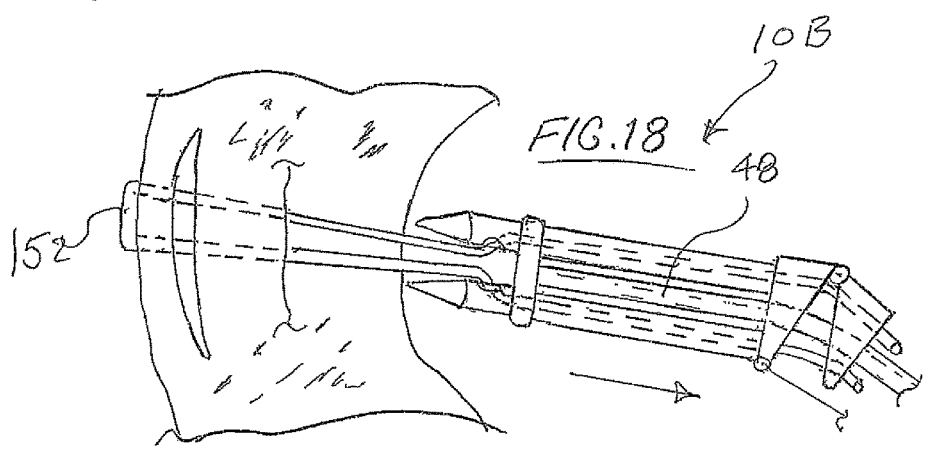
FIG. 18 is a schematic top plan view of the device of FIG. 10 in which the repaired suture has been placed across the meniscal tear.
Figure 21:
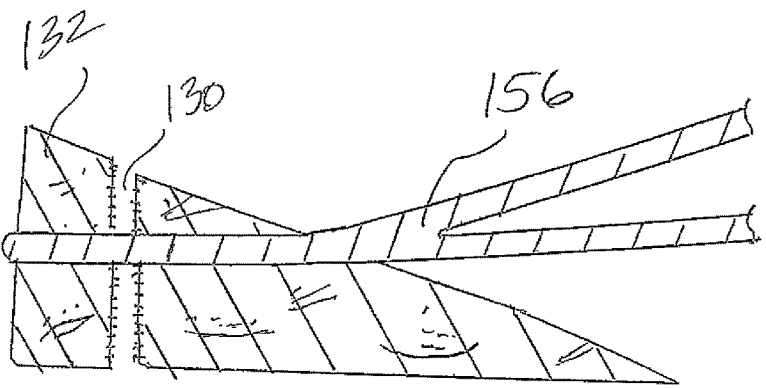
FIG. 21 is a sectional view showing the placement of a repair suture across a meniscal tear in a generally horizontal position.
Figure 22:
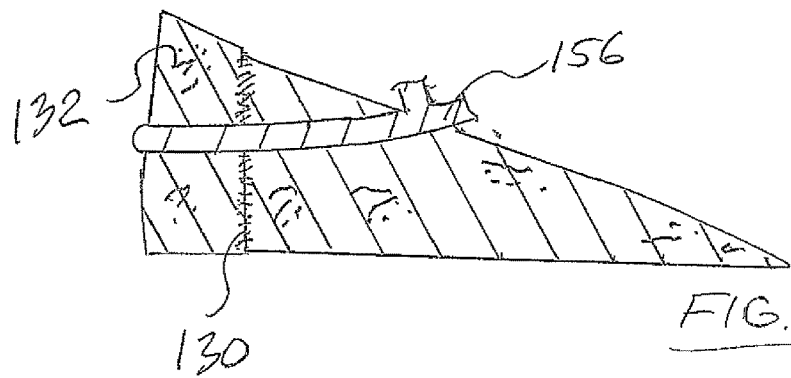
FIG. 22 is a sectional view showing the knotted repair suture of FIG. 21.
Figure 23:
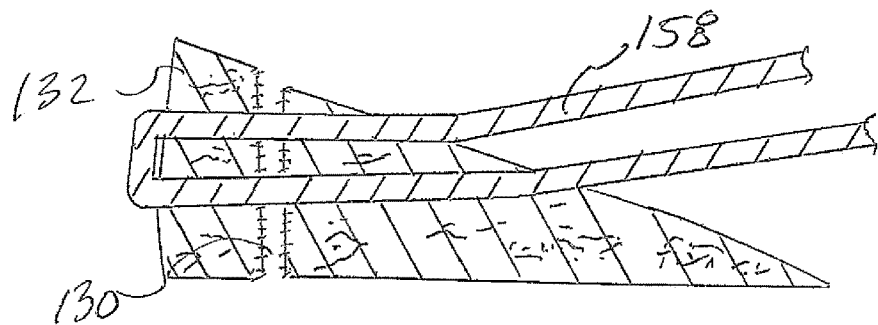
FIG. 23 is a sectional view showing the placement of a generally vertical repair suture across a meniscal tear.
Figure 24:
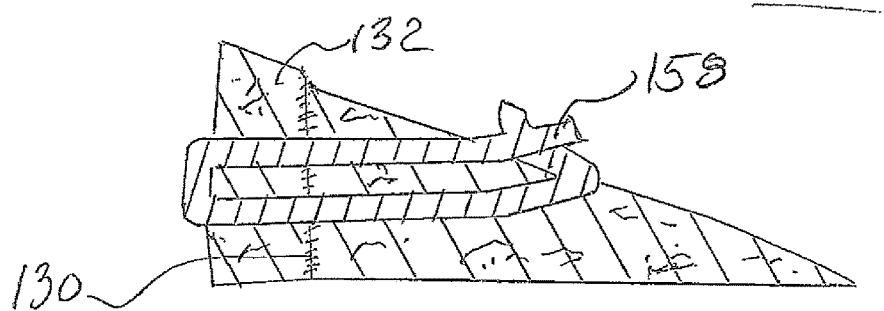
FIG. 24 is a sectional view showing the knotted repair suture of FIG. 23.

Using embodiment 10B shown in FIGS. 10, 13A and 13B, the user positions device 10B within the knee joint and in a position adjacent tear 130 adjacent meniscus 144, FIG. 13. It should be noted that the device 10B is capable of rotating counter clockwise and may be employed with meniscus 132 on the left in FIG. 13. However, if a tear were to be repaired in meniscus 144 at the right in FIG. 13, device 10B would require hinge 62 to be reversed on support 56 to allow clockwise rotation of first and second portions 58 and 60. Thus, separate right and left angulation devices of the present invention are required to repair tears of all menisci. Angulation of device 10B is adjusted using angle operator shaft 82. It should be noted that greater angulation is generally required for tears that are more anterior in a meniscus. Nerves and other sensitive structures should be kept out of the path of the components of device 10B namely, cannula 40 and 42 and elongated pulling element 50. As depicted in FIG. 13, tear 130 constitutes a mid-body tear. Once device 10B is adjacent upper surface 146 of meniscus 132, FIG. 14 elongated pulling element 50 is then advanced across tear 130 above meniscus 132 or through meniscus 132, as the case may be. Proper alignment of device 10B is then confirmed prior to further needle advancement. When proper alignment is achieved, needle 52 is passed outside the knee joint periphery 148. Thus, needle 152 lies the knee. Needle 152 is then detached and discarded, allowing access to line 54 which is pulled or kedged. At this point, knot 38 engages first portion 58 of support 56, FIG. 14. Directional arrow 150 indicates such pulling or traction. Steady traction is applied to device 10B to advance cannula 40 and 42 along the desired depth and direction into meniscus 132 under careful observation, of the surgeon, FIG. 15. Repair suture 152 is then guided through tube 72, cannula 42, cannula 40 and tube 70 by known methods in the prior art, FIG. 16. Push-pull bar 48 is now advanced to eject cannula 40 and 42 from meniscus 132, directional arrow 154, FIG. 17. The angulation of device 10B may then be released to facilitate its removal from the knee joint by deactivating lock 84, shown schematically on FIG. 10. Once device 10B is removed, repair suture 152 is tensioned, tied, and trimmed. It should be noted that suture repairs may be effected by device 10C and device 10D in the same manner, except that device 10D produces a vertical suture repair. That is to say, with reference to FIGS. 21 and 24, devices 10A, 10B, and 10C would effect a generally horizontal repair, depicted in FIGS. 21 and 22 with suture 156, of tear 130 in meniscus 132. Likewise, device 10D having a hinge 110 turned 90 degrees relative to hinge 62 and device 10B would effect a vertical repair, shown in FIGS. 23 and 24 with respect to repair suture 158.

Figure 25:
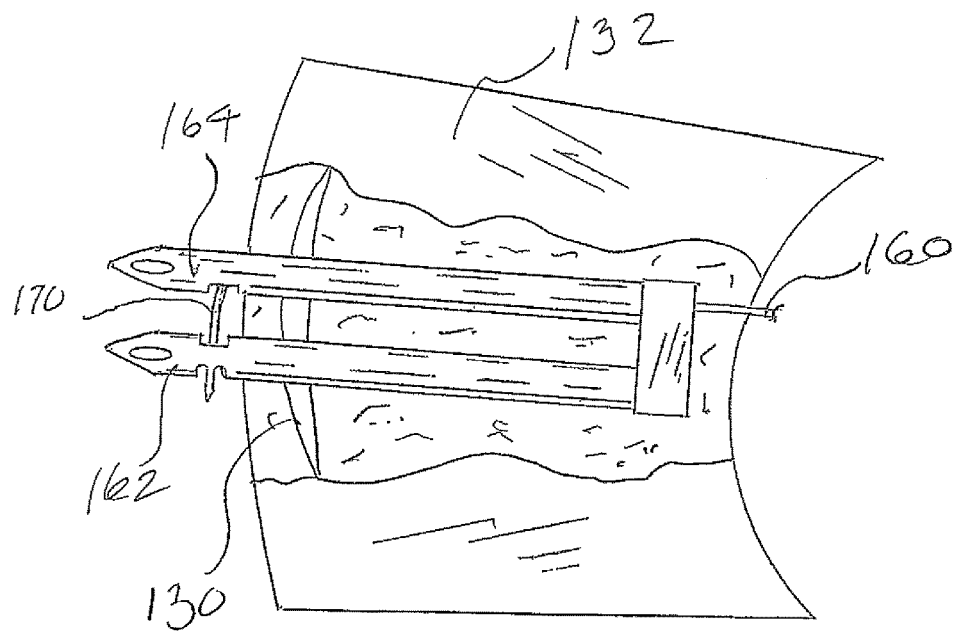
FIG. 25 is a schematic top plan view of the present invention depicting a high exit angle transfer of the repair suture between a pair of cannulas to repair a meniscus tear.
Figure 26:
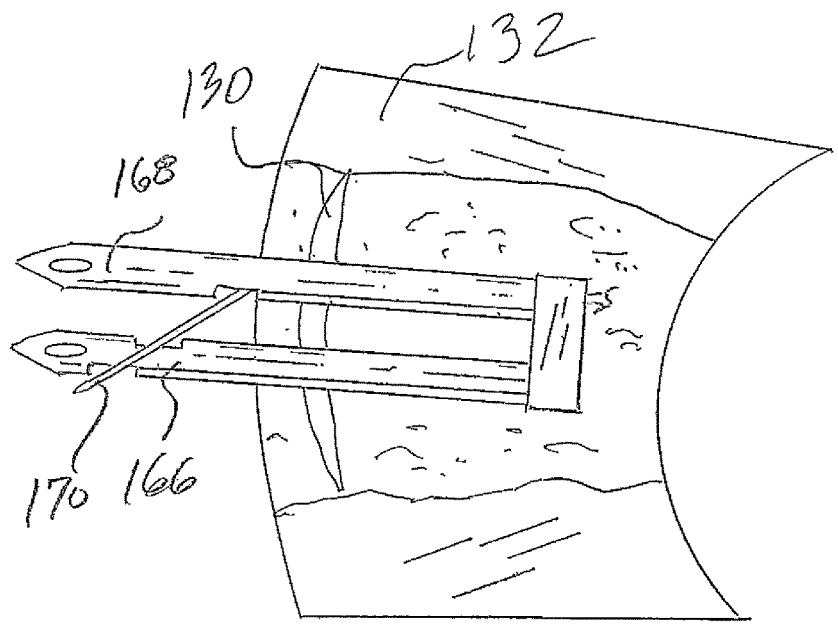
FIG. 26 is a schematic top plan view showing a pair of cannulas exhibiting a low exit angle of transfer of the repair suture across the meniscal tear.

FIGS. 25 and 26 show typical structures for a pair of cannulas passing a repair suture 160. As shown in FIG. 25, cannula 162 and 164 pass repair suture 170 generally across, using the cannula suture openings depicted. FIG. 26 shows cannulas 166 and 168 in which repair suture 170, is passed at an angle, since the openings in cannula 166 and 168 are offset.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A system for repairing a tear in a meniscus of a knee joint, the system comprising:
   a suturing component comprising a first cannula and a second cannula connected by at least one support, the suturing component capable of being introduced into the knee joint at an entry point and moved to a first location within the knee joint by pushing, the suturing component capable of delivering a suture line; and
   a pulling component movably connected to the suturing component, the pulling component capable of exiting the knee joint at an exit point different from the entry point, the pulling component comprising a traction line which is different from the suture line, the pulling component further capable of providing for the suturing component to be pulled from the first location to a second location within the knee joint proximate the meniscus tear using the traction line;
   wherein after the suturing component is pulled into the second location using the traction line of the pulling component, the suturing component capable of being used to make a suture of the meniscus tear by transferring a repair suture from the first cannula to the second cannula, the repair suture formed from the suture line.

2. The system of claim 1, wherein the exit point is non-linear with respect to the position of the suturing component as the suturing component is introduced into the knee at the entry point.

3. The system of claim 1 wherein the support comprises passageways for the first and second cannulas, the passageways for the first and second cannulas being sized to permit sliding of the first and second cannulas relative to the support.

4. The system of claim 3 wherein the pulling component further comprises a rigid pointed member connected to the traction line, the rigid pointed member capable of creating an opening at the exit point and advancing the traction line through the exit point.

5. The system of claim 4, wherein the exit point is non-linear with respect to the position of the suturing component as the suturing component is introduced into the knee at the entry point.

6. The system of claim 4 in which said rigid pointed member comprises a needle.

* * * * *